US00PP09588P

United States Patent [19]

Endisch et al.

[11] Patent Number: Plant 9,588

[45] Date of Patent: Jun. 18, 1996

[54] GERANIUM PLANT NAMED 'VIGO'

[75] Inventors: Gerd Endisch, Geranienweg, D-76767, Hagenbach; Ursula Endisch-Burmeister, Bad Kreuznach, both of Germany; Wolf Endisch, Valle Guerra, Teneriffa, Spain

[73] Assignee: Gerd Endisch, Hagenbach, Germany

[21] Appl. No.: 399,993

[22] Filed: Feb. 6, 1995

[30] Foreign Application Priority Data

May 25, 1994 [DE] Germany ..... PEL 981

[51] Int. Cl.[6] ..... A01H 5/00

[52] U.S. Cl. ..... Plt./87.12

[58] Field of Search ..... Plt./87.12

*Primary Examiner*—James R. Feyrer

*Attorney, Agent, or Firm*—Willian Brinks Hofer Gilson & Lione

[57] ABSTRACT

A new and distinct cultivar of geranium known by the cultivar name 'Vigo' is characterized by a salmon flower color, a semi-double flower form, very strong zonation, medium green foliage, a compact habit and an early flower response.

1 Drawing Sheet

BACKGROUND OF THE NEW PLANT

The present invention comprises a new and distinct cultivar of geranium botanically known as *Pelargonium zonale*, and hereinafter referred to by the cultivar name 'Vigo'. 'Vigo' is a product of planned breeding program which had the objective of creating new geranium cultivars with salmon flower color, strong zonation, semi-double flower form, compact habit.

'Vigo' was originated from a hybridization made in a controlled breeding program in Hagenbach, Germany, in 1991. The female parent was 'Erfolg', characterized by its salmon flower color, semi-double flower form, strong zonation, medium green foliage and small umbels. 'Erfolg' is not patented and is no longer commercially available. The male parent of 'Vigo' was 'Unica', characterized by its salmon-pink flower color, semi-double flower form, dark foliage without zonation, late flower response. In addition to the distinguishing characteristics noted above, 'Vigo' has dark foliage with strong zonation and an early flower response. 'Unica' was patented in Germany but is no longer commercially available.

'Vigo' was discovered and selected as one flowering plant within the progeny of the stated cross by the inventors in September 1992 in a controlled evvironment in Hagenbach, Germany.

DESCRIPTION OF THE NEW PLANT

The first act of asexual reproduction of 'Vigo' was accomplished when vegetative cuttings were taken from the initial selection in January 1993 in a controlled environment in Hagenbach, Germany, by a technician working under formulations established and supervised by Gerd Endisch.

Horticultural examination of selected units initiated in May 1993 has demonstrated that the combination of characteristics as herein disclosed for 'Vigo' are firmly fixed and are retained through successive generations of asexual reproduction.

'Vigo' has not been observed under all possible environmental conditions. The phenotype may vary significantly with variations in environment such as temperature, light intensity, and day length. The following observations, measurements, and comparisons describe plants grown in Hagenbach, Germany, under field conditions which approximate those generally used in commercial practice. All measurements and dimensions given below are approximate.

The following traits have been repeatedly observed and are determined to be basic characteristics of 'Vigo' to distinguish this geranium as a new and distinct cultivar:

1. salmon flower color
2. semi-double flower form
3. very strong zonation
4. medium green foliage
5. compact habit
6. early flower response Of the many commercial cultivars known to the present inventor, the most similar in comparison to 'Vigo' is 'Erfolg'. Reference is made to Chart A below which compares certain characteristics of 'Vigo' to those same characteristics of 'Erfolg'. In comparison to 'Erfolg', 'Vigo' has a larger umbel, earlier flower response and a compact habit.

BRIEF DESCRIPTION OF THE DRAWINGS

The accompanying photographic drawing(s) show typical flower and foliage characteristics of 'Vigo', with colors being as true as possible with illustrations of this type.

DETAILED BOTANICAL DESCRIPTION

In the following description color references are made to The Royal Horticultural Society Colour Chart (RHS). The color values were determined indoors from plants grown outdoors in August 1994 in Hagenbach, Germany, or Hannover (Bundessortenamt).

Classification:

*Botanical.*—A hybrid of the species *Pelargonium zonale.*

*Commercial.*—Zonal geranium, cv. 'Vigo'.

INFLORESCENCE

Umbel: Comprises approx. 55 flowers.

*Average diameter.*—Approx. 93 mm.

*Average depth.*—Approx. 48–50 mm.

*Peduncle length.*—Approx. 160 mm.

*Spring flowering response period.*—In Hannover, Germany, 1994 (Bundessortenamt) first flower April 5.

*Outdoor flower production.*—The flower count in 1993 indicated between 70–75 flowers per plant for May 15 through August 15 observation period.

*Durability.*—Medium rain resistance good heat resistance.

Corolla:

*Blooming habit.*—Continuous (until frost destroys plant).

*Average diameter.*—Approx. 40–42 mm.

*Form.*—semi-double, flat to slightly cupped.

*Petals.*—Approx. 7–9, approx. 19 mm across.

*Color.*—(General tonality from a distance of three meters) salmon.

*Color of upper surface.*—RHS 48 D margin, RHS 48 B middle.

*Color of bottom surface.*—RHS 49 A.

*Pedicel length.*—Approx. 26–28 mm.

*Pedicel color.*—Red (anthocyanin colored).

Bud:

*Size.*—Approx. 8 mm across.

*Shape.*—Elliptic.

*Sepals.*—Approx. 5, pointed linear lanceolate; at time of opening of petal, approx. 9 mm length.

*Color.*—Green with anthocyanin at the base.

Reproductive organs:

*Stamens.*—Anthers: 5–8 anthers with orange/red pollen. Filaments: Approx. 6–8 mm in length.

*Pistil.*—No.: One. Length: Approx. 9 mm. Stigma: 5 lobes, red colored. Style: Approx. 3 mm in length; red.

*Ovaries.*—Green.

*Fruit.*—Partially fertile.

PLANT

Foliage: Abundant quantity; leaves with strong zonation.

*Size.*—Approx. 10–11 cm across.

*Form.*—Kidney shaped, Type I (UPOV).

*Margin.*—Bicrenate.

*Texture.*—Leathery.

*Ribs and reins.*—Palmate venation.

*Color (upper surface).*—RHS 137 B; zonation: RHS 147 A, strong.

*Color (bottom surface).*—RHS 137 C.

Petioles: Approx. 8–10 cm in length; green.

General appearance and form: Bushy, compact.

*Internode length.*—Approx. 22–24 mm.

*Branching pattern.*—Self-branching, 22 branches observed 15 Aug. 1994.

*Height.*—Approx. 18–29 cm from media surface.

*Strength.*—Early flower response and fast rooting.

Chart A

| | New Cultivar Name: 'Vigo' | Comparison Cultivar Name: 'Erfolg' |
|---|---|---|
| Umbel | larger | smaller |
| Flower response | earlier | later |
| Corolla | bigger | smaller |

What is claimed is:

1. A new and distinct cultivar of geranium plant known as 'Vigo', as described and illustrated and particularly characterized by a salmon flower color, a semi-double flower form, very strong zonation, medium green foliage, a compact habit and an early flower response.

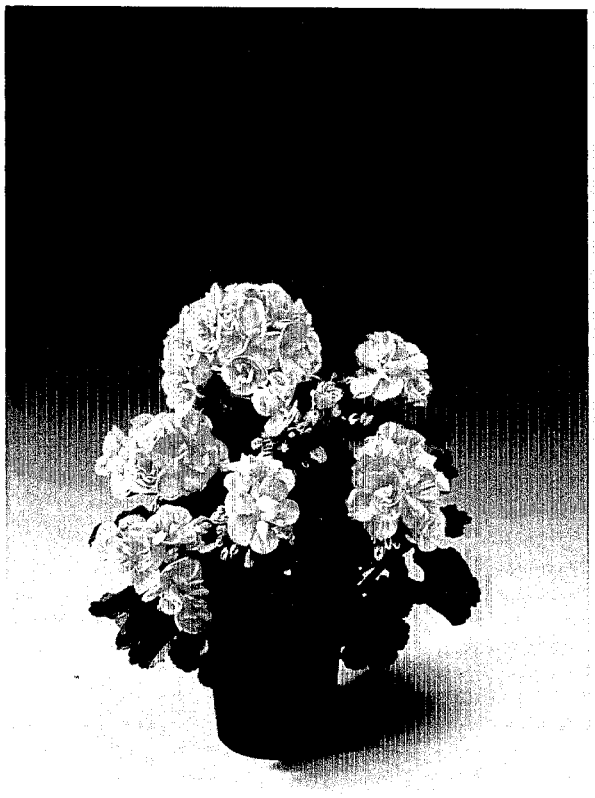

* * * * *